US008838229B2

(12) United States Patent
Gibson et al.

(10) Patent No.: US 8,838,229 B2
(45) Date of Patent: Sep. 16, 2014

(54) METHOD AND DEVICE FOR ELECTROMOTIVE DELIVERY OF MACROMOLECULES INTO TISSUE

(75) Inventors: Daniel J. Gibson, Gainesville, FL (US); Sonal S. Tuli, Gainesville, FL (US); Gregory S. Schultz, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 313 days.

(21) Appl. No.: 13/318,916

(22) PCT Filed: May 4, 2010

(86) PCT No.: PCT/US2010/033551
§ 371 (c)(1),
(2), (4) Date: Dec. 12, 2011

(87) PCT Pub. No.: WO2010/129552
PCT Pub. Date: Nov. 11, 2010

(65) Prior Publication Data
US 2012/0078162 A1 Mar. 29, 2012

Related U.S. Application Data

(60) Provisional application No. 61/175,331, filed on May 4, 2009.

(51) Int. Cl.
*A61N 1/30* (2006.01)
*A61N 1/04* (2006.01)

(52) U.S. Cl.
CPC ............ *A61N 1/303* (2013.01); *A61N 1/0424* (2013.01); *A61N 1/0448* (2013.01); *A61N 1/044* (2013.01)
USPC .......................................... 604/21

(58) Field of Classification Search
CPC .......... A61N 1/30; A61K 9/22; A61K 49/00; A61M 37/00
USPC ...................................... 604/19, 20, 289, 294
See application file for complete search history.

(56) References Cited

U.S. PATENT DOCUMENTS

2006/0116641 A1 6/2006 Gordon et al.
2006/0211980 A1 9/2006 Cormier et al.
(Continued)

OTHER PUBLICATIONS

Gibson, D.J. "Electromotive Delivery of Oligonucleotides Into the Cornea." Graduate Thesis, 2007, University of Florida.
(Continued)

*Primary Examiner* — Manuel Mendez
(74) *Attorney, Agent, or Firm* — Saliwanchik, Lloyd & Eisenschenk

(57) ABSTRACT

Electromotive delivery of macromolecules can be provided using a delivery device including a first chamber for contacting a macromolecule delivery medium to a surface of a tissue or other anatomy of a patient; and a second chamber for contacting a receiving medium to the patient. A first electrode can be disposed in the first chamber so as to not directly contact the macromolecule delivery medium. A second medium having a buffering agent can be used to keep the first electrode from coming into direct contact with the macromolecule delivery medium. A second electrode can be disposed within the receiving medium in the second chamber such that the second electrode does not directly contact the patient. An electric field can be generated using the first and second electrodes in order to cause the macromolecule delivery medium to move into the tissue of interest from the first chamber of the delivery device.

42 Claims, 16 Drawing Sheets

(56) References Cited

U.S. PATENT DOCUMENTS

2006/0264807 A1  11/2006  Westersten et al.
2007/0081944 A1   4/2007  Reed
2007/0093787 A1   4/2007  Smith
2009/0048556 A1   2/2009  Durand

OTHER PUBLICATIONS

Gibson, D.J., et al., "High Field Computer Controlled Pulse Iontophoresis of Oligonucleotides Into the Cornea," presentation, Spring 2006, University of Florida.

Gibson, D.J., et al., "Optimization of Electrode Material and Placement for In-Vivo Iontophoretic Delivery of Oligonucleotides into the Stroma," presentation, Apr. 29, 2008, University of Florida.

Gibson, D.J., et al., "Trans-corneal HEPES Buffered Iontophoresis for Delivery of Oligonucleotides Into the Stroma," presentation, Spring 2007, University of Florida.

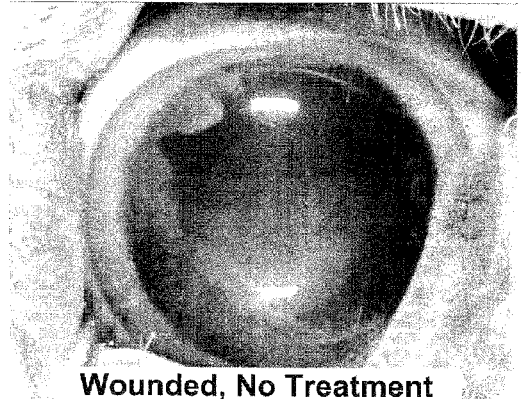
FIG. 12A Wounded, No Treatment
FIG. 12B Not Wounded, No Treatment
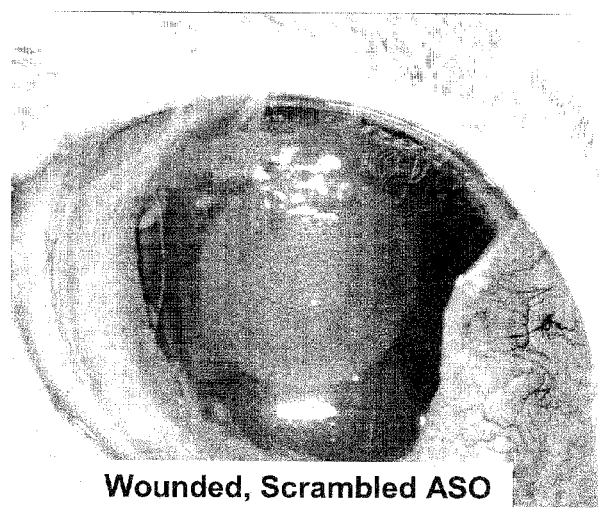
FIG. 12C Wounded, Scrambled ASO
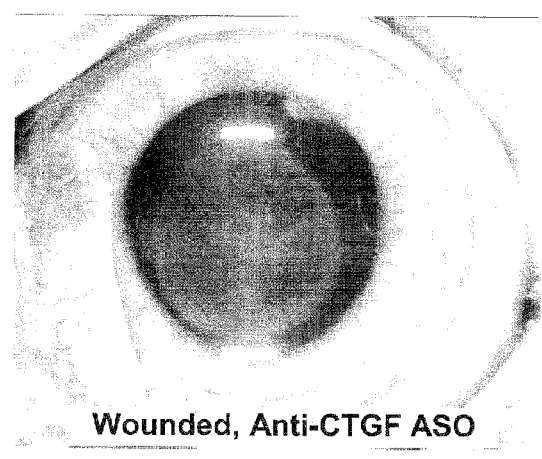
FIG. 12D Wounded, Anti-CTGF ASO

METHOD AND DEVICE FOR ELECTROMOTIVE DELIVERY OF MACROMOLECULES INTO TISSUE

CROSS-REFERENCE TO RELATED APPLICATIONS

The present application is the U.S. National Stage Application of International Patent Application No. PCT/US2010/033551, filed on May 4, 2010, which claims the benefit of U.S. Provisional Application Ser. No. 61/175,331, filed May 4, 2009, both of which are hereby incorporated by reference herein in their entirety, including any figures, tables, or drawings.

BACKGROUND OF INVENTION

Short polymers of nucleic acids termed oligonucleotides have the capability to silence protein production by either modifying or degrading the messenger ribonucleic acid (mRNA) template rendering it untranslatable. These oligonucleotides have potential therapeutic applications if they are targeted to deleterious endogenous genes, or even exogenous bacterial or viral genes. In order to be effective, the oligonucleotides need to be delivered into the cytoplasm (ribozymes and deoxyribozymes) or into the nucleus (short-interfering ribonucleic acid (siRNA) and micro-interfering ribonucleic acid (miRNA)). A method of delivery using electromotive force to drive the highly charged oligonucleotides from an external delivery solution into the cornea is referred to as iontophoresis. Iontophoresis has been used to deliver small ionic drugs into the cornea. Because nucleic acids are significantly larger than small ionic drugs, high doses of electricity can be needed to effect delivery. Although the process of iontophoresis dates back to the early 1900's, the process has not been understood well enough for efficacious macromolecular drug delivery without significant tissue damage.

BRIEF SUMMARY

Embodiments of the subject invention relate to a method and apparatus for electromotive delivery of macromolecules into tissue. Specific embodiments pertain to electromotive delivery of macromolecules into corneas, skin, hair, and/or finger or toe nails, and/or internal tissues.

In accordance with one embodiment, a device for electromotive delivery of macromolecules is provided that includes: a first chamber having a first distal end for contact with a patient, wherein the first distal end of the first chamber allows a macromolecule delivery medium in the first chamber contact with the patient; a second chamber connected to the first chamber by a connector, wherein the second chamber has a second distal end for contact with the patient, wherein the second distal end of the second chamber allows a receivable medium in the second chamber contact with the patient; a first electrode in the first chamber; and a second electrode in the second chamber. The second chamber and the first chamber can be separated by a wall.

In certain embodiments, the second chamber is concentric to the first chamber such that the wall separating the first chamber from the second chamber is the wall defining the sides of the first chamber. In another embodiment, the first chamber and the second chamber are disposed side-by-side with a common wall that separates the chambers. In yet another embodiment, the first chamber can be a needle and the second chamber can be formed by a space created between a protective layer and the outer wall of the needle.

The first electrode can be separated from delivery medium in the first chamber by a buffering agent in contact with the first electrode, and the second electrode can be in contact with a receivable medium in the second chamber. The electrodes can be arranged such that when a voltage is applied across the first and second electrodes, an electric field contour is created that originates at the first electrode, passes through the buffering agent, passes through the delivery medium, passes into the tissue, travels in a curved path that includes a lateral component, passes out of the tissue at a laterally offset position from where the electric field contour entered the tissue, and through the receivable medium to the second electrode.

In accordance with an embodiment, a method of delivering macromolecules to a tissue is provided that includes: contacting a macromolecule delivery medium disposed in a first chamber of a delivery device to a patient, and contacting a receivable medium disposed in a second chamber of the delivery device to the patient; applying power to a first electrode disposed in the first chamber of the delivery device and a second electrode disposed in the second chamber to create an electric field having a contour along a path from the first electrode through the macromolecule delivery medium to the patient into the tissue and passing out of the tissue through the receivable medium to the second electrode, whereby the electric field causes macromolecules from the macromolecule delivery medium to be directed to the tissue.

The power can be applied by voltage or current control using constant, pulsed, ramped, and/or custom voltage or current vs. time profiles. Embodiments of the device can include distinct sets of electrodes with differing functions. For example, while one set of electrodes is used to deliver the deliverable into the tissue, a second set of electrodes can be present in a different location to electroporate the tissue post-delivery in order to improve the cellular uptake of the deliverable.

BRIEF DESCRIPTION OF DRAWINGS

The file of this patent contains at least one drawing executed in color. Copies of this patent with color drawings will be provided by the Patent and Trademark Office upon request and payment of the necessary fee.

FIG. 8A shows 44.0 µm ablation with no applied treatment; FIG. 8B shows 100.7 µm ablation with 0.0 mA of current applied for 5 min; FIG. 8C shows 119.3 µm ablation with 1.0 mA of current applied for 5 min; FIG. 8D shows 84.3 µm ablation with 1.5 mA of current applied for 5 min; FIG. 8E shows, at a 10× resolution, 53.6 µm ablation with 2.0 mA of current applied for 5 min using a dose of 100 µl; FIG. 8F shows the result of FIG. 6E at a 40× resolution; FIG. 8G shows, at a 10× resolution, 54.8 µm ablation with 3.0 mA of current applied for 5 min using a dose of 2×45 µl; FIG. 8H shows the result of FIG. 8G at a 40× resolution; FIG. 8I shows an image of the edge of the result of FIG. 8G; FIG. 8J shows an image of the center of the result of FIG. 8G; FIG. 8K shows an image of the edge of the result after 4.0 mA of current was applied for 5 min; FIG. 8L shows an image of the center of the result after 4.0 mA of current was applied for 5 min.

FIGS. 12A-12D show images of the eyes of a control rabbit (A,B) and a rabbit receiving iontophoretically delivered scrambled ASO (C), or anti-CTGF ASO (D).

DETAILED DISCLOSURE

Embodiments of the subject invention relate to a method and apparatus for electromotive delivery of macromolecules into tissue. Specific embodiments pertain to electromotive delivery of macromolecules into corneas, skin, hair, and/or finger or toe nails, and/or internal tissues.

Figure 1A:
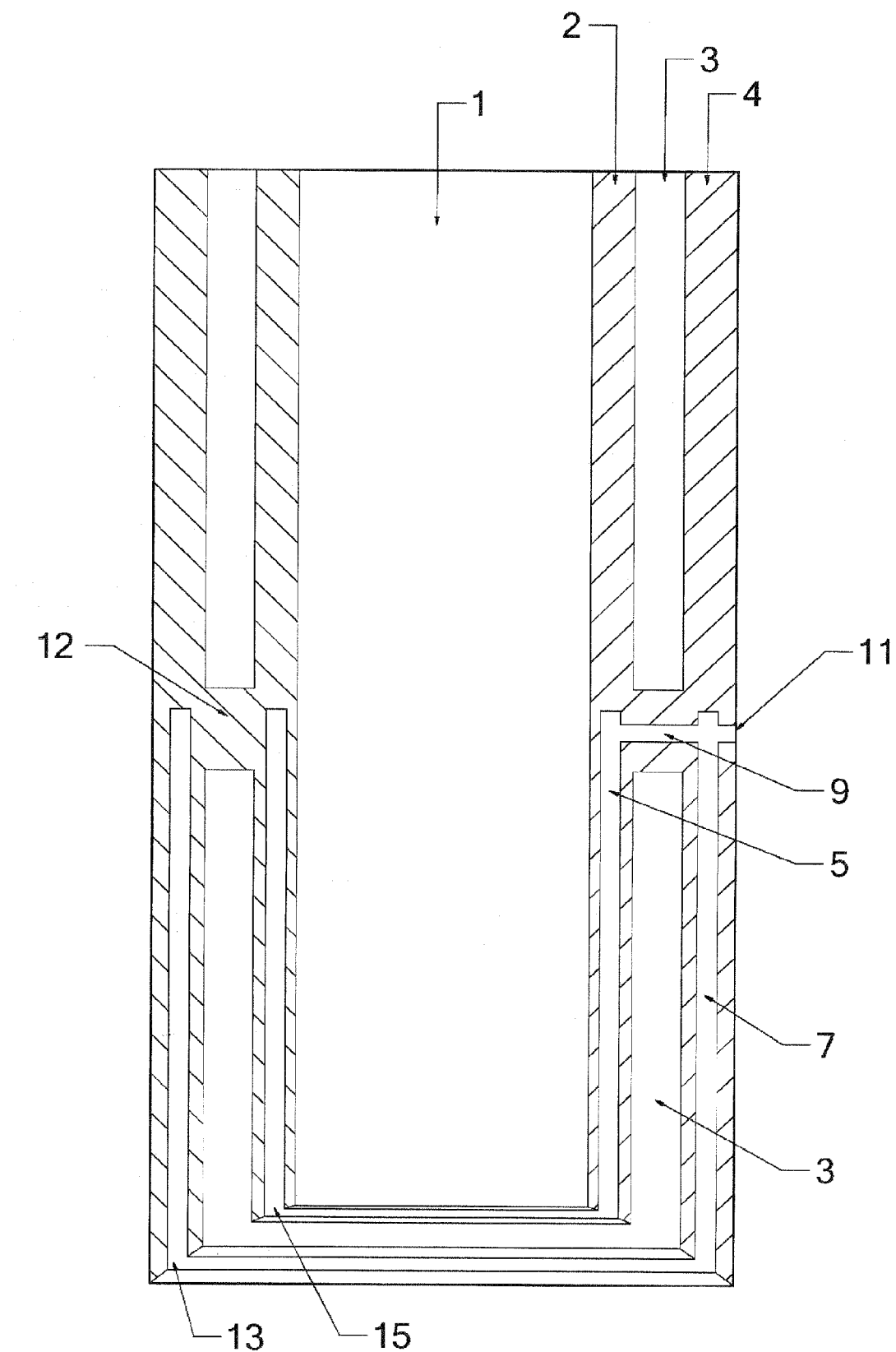
FIG. 1A shows a longitudinal cross-section of a device for delivery of macromolecules in accordance with an embodiment of the subject invention.
Figure 1B:
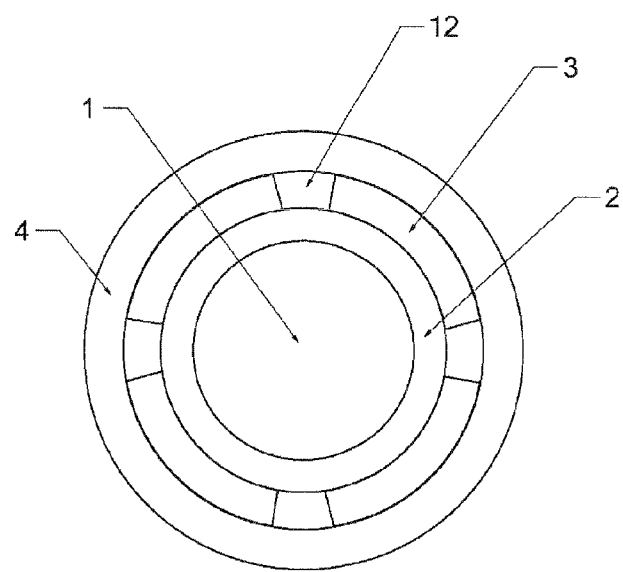
FIG. 1B shows a radial cross-section of a device for delivery of macromolecules in accordance with an embodiment of the subject invention.

FIG. 1A shows a longitudinal cross-section of a device for electromotive delivery of macromolecules into tissue, and FIG. 1B shows a radial cross-section of a device for electromotive delivery of macromolecules into tissue. The device incorporates a central chamber 1 for positioning a medium with the deliverable macromolecules. In a specific embodiment, a first medium with the deliverable macromolecules can be located at one end of the central chamber 1 for contact with the tissue and a second medium can be located on top of the first medium such that a first electrode is in contact with the second medium and not in contact with the first medium. In a specific embodiment, the second medium incorporates an immobilized buffer, preventing or reducing the movement or migration of the second medium into the first medium. As an example, a buffering agent such as poly histidine polymer can be used. The device can also have a second chamber for locating a receivable medium.

The second chamber 3 shown in FIGS. 1A and 1B is an annular chamber 3 that is concentric to the central chamber 1. Wall 2 separates the central chamber 1 and the second chamber 3 and wall 4, along with wall 2, forms the second chamber 3. Spokes 12 can connect the walls 2 and 4 of the chambers. The spokes 12 can be formed of the same material as the walls 2 and 4, and may be formed as part of the walls. In a specific embodiment, the walls and spokes can be formed of a non-conducting material. The spokes 12 are configured so as to allow flow between the portion of the second chamber 3 above the spokes 12 and the portion of the second chamber 3 below the spokes 12. The spokes 12 may be disposed at intervals along the longitudinal direction and/or in the axial direction. The shape of the spokes 12 can be selected so as to minimize gas accumulation. For example, tubular spokes having a curved circumference can be used. In certain embodiments, one or more of the spokes 12 can include conduits for fluid flow into and/or out of the central chamber 1. In an embodiment, one or more of the spokes 12 can include a conduit 9 for applying a vacuum. Two vacuum chambers 5 and 7 formed in walls 2 and 4, respectively, allow a vacuum to be applied at aperture 11 and through conduit 9 to suction devices 15 and 13, respectively, for creating a suction seal of the device with the tissue in order to reduce or prevent leakage of the materials from chambers 1 and/or 3. These vacuum chambers can be concentric with the central chamber or can be other shapes that allow the vacuum to reach the suction devices. The vacuum may be applied at aperture 11 using, for example, a vacuum syringe. In certain embodiments, other suction or attachment devices can be used that do not require a vacuum chamber.

The device shown in FIG. 1A has a curved contact structure for contacting a cornea, where other shapes for the contact structure can be used for other tissues.

A second electrode can be in contact with the receivable medium such that a voltage can be applied across the first and second electrode so as to create an electric field contour that originates at the first electrode, passes through the second medium, passes through the deliverable medium, passes into the tissue, travels in a curved path that includes a lateral component, passes out of the tissue at a laterally offset position from where the electric field contour entered the tissue, and through the receivable medium to the second electrode.

In a specific embodiment, the receivable medium incorporates an immobilized buffer where the receivable material is bound to a matrix or other structure, such as cotton or a gel, that prevents or reduces the movement of receivable medium in response to the electric field created by the voltage applied across the first and second electrodes. As an example, a buffering agent such as a poly histidine polymer can be used. In one embodiment, the outer chamber is created by a host matrix structure, such as cotton or gauze, that holds the immobilized buffer, and an outer wall (e.g., 4 of FIG. 1A) can be omitted.

A high enough electric field needs to be produced to surmount a threshold for delivery of the macromolecule into the tissue, without destroying the tissue.

Aspects of various embodiments of the invention include one or more of the following: controlling the ionic strength (resistivity) of the delivery solution, keeping the ionic strength low (high resistivity); having a sufficient buffering capacity to neutralize the OH− and H+ generated by electrolysis; and using a buffering agent having a low electrophoretic mobility (high mass to charge ratio). The low electrophoretic mobility of the buffering agent may be a naturally occurring characteristic of the buffering agent or due to physical immobilization of the buffering agent to a medium. Balancing these variables can be important, since the high ionic strength (low resistivity) can prevent delivery, as can having a buffering agent that is too mobile (since it may be delivered instead of the drug). In addition, too low of a buffering capacity can lead to the delivery solution becoming caustic, which can cause catastrophic tissue destruction. In a specific embodiment, a buffering agent that is tightly bound (either covalent or highly hydrophobically bound) to a gel or matrix that is between the electrodes and the body/drug can be utilized.

In a specific embodiment, the electrodes can be placed as close as the situation permits. The volume of the delivery medium (first medium) can affect the spacing of the electrodes. An electrode geometry that is conducive to generating a homogenous/symmetric delivery area can be used.

Figure 1C:
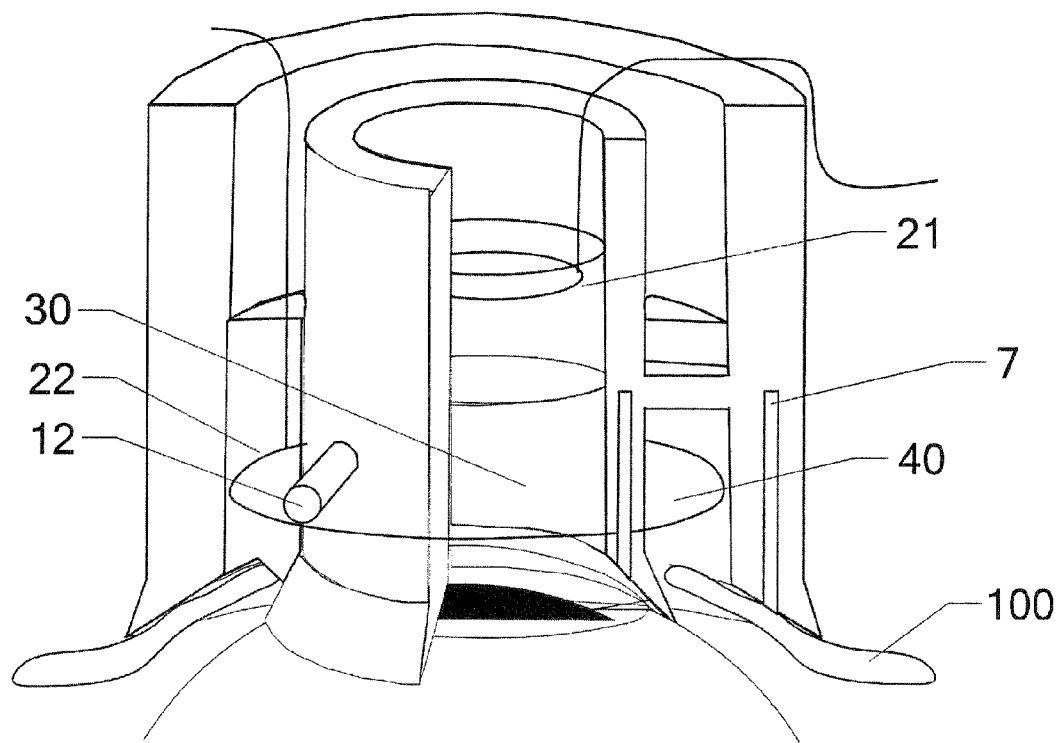
FIG. 1C shows application of a device for delivery of macromolecules in accordance with an embodiment of the subject invention.

In a specific embodiment, such as shown in FIG. 1C, concentric electrodes 21, 22 can be electrically connected with a patient's body through the delivery solution 30 and by a buffer soaked matrix 40 in contact with the outer eye lid 100 for transcorneal delivery. In one embodiment, the electrodes 21 and 22 can be formed of, or include, platinum. The vacuum chambers, such as chamber 7 in the outer wall, can be used to create a suction seal between the outer wall and the outer eye lid and the inner wall and the cornea. Spokes 12 are used to connect the two walls while minimizing gas accumulation. The spokes can be arranged in the outer chamber at intervals. For embodiments having the vacuum chambers, one or more of the spokes 12 can include a conduit 9 for applying a vacuum. Embodiments can be used for delivery in other tissues as well.

A delivery solution that is composed of multiple phases of varying densities can also be used, which can allow for the drug to be placed in a dense solution that will sink to the bottom of the delivery chamber and come into conforming contact with the tissue. This can ensure effective contact between the drug solution and the tissue without any pressure above the hydrostatic pressure of the fluid column. In addition, the drug in the dense solution can be equally distributed across the tissue. Further, the drug in the dense solution that sinks to the bottom of the delivery chamber decreases the distance that the drug has to travel to become "delivered". Finally, by sinking the drug onto the tissue, the drug is prevented from being oxidized/reduced by the electrode, depending on the molecule being delivered, which can prevent or reduce modifications to the drug molecule and cause unexpected side effects.

Embodiments of the invention can allow the delivery of molecular biological agents such as plasmids, siRNA, ribozymes and aptamers.

A specific embodiment pertains to a self contained handheld unit with an integrated power supply, immobilized buffering agent coating/wrapped around the electrodes, and an electrical path that has as small portion of the patient in the circuit.

Figure 2:
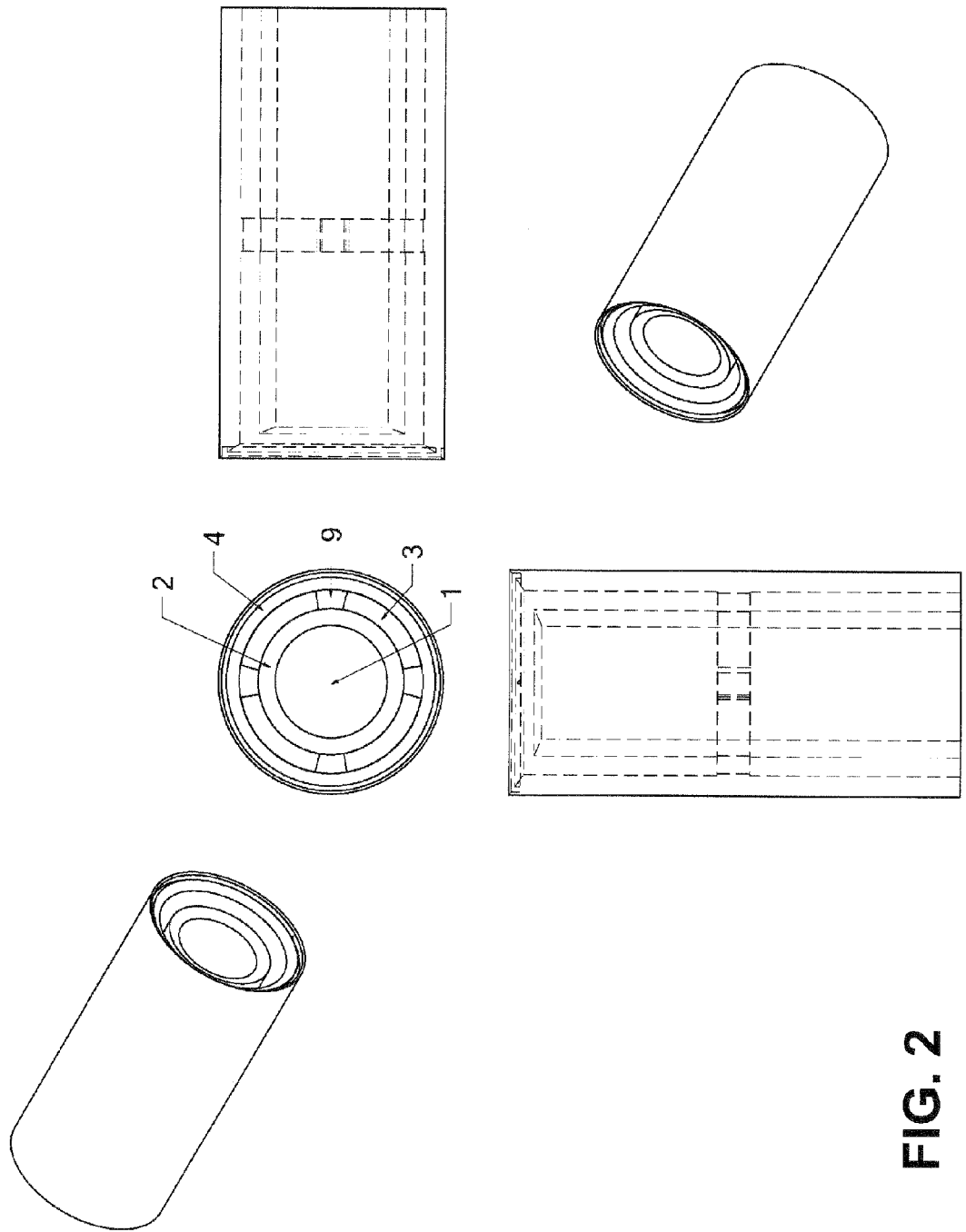
FIG. 2 shows an end view, two perspective views, and two longitudinal views of a device for delivery of macromolecules in accordance with an embodiment of the invention.

FIGS. 1 and 2 show devices designed for use with circular, concentric electrodes. In further embodiments, the device's electrodes may be individual monolithic electrodes, or an array of independently controlled electrodes which would allow the distribution (i.e., shape) of the electric field to be controlled. An example includes fine tuning the shape of the electric field to smooth out any heterogeneities in the delivery field (i.e., to ensure a homogenous delivery into the area of interest). The electrode array can be arrayed in two or three dimensions. Embodiments of the device may have distinct sets of electrodes with differing functions. For example, while one set of electrodes is used to deliver the deliverable into the tissue, a second set of electrodes can be present in a different location to electroporate the tissue post-delivery in order to improve the cellular uptake of the deliverable.

Figure 3:
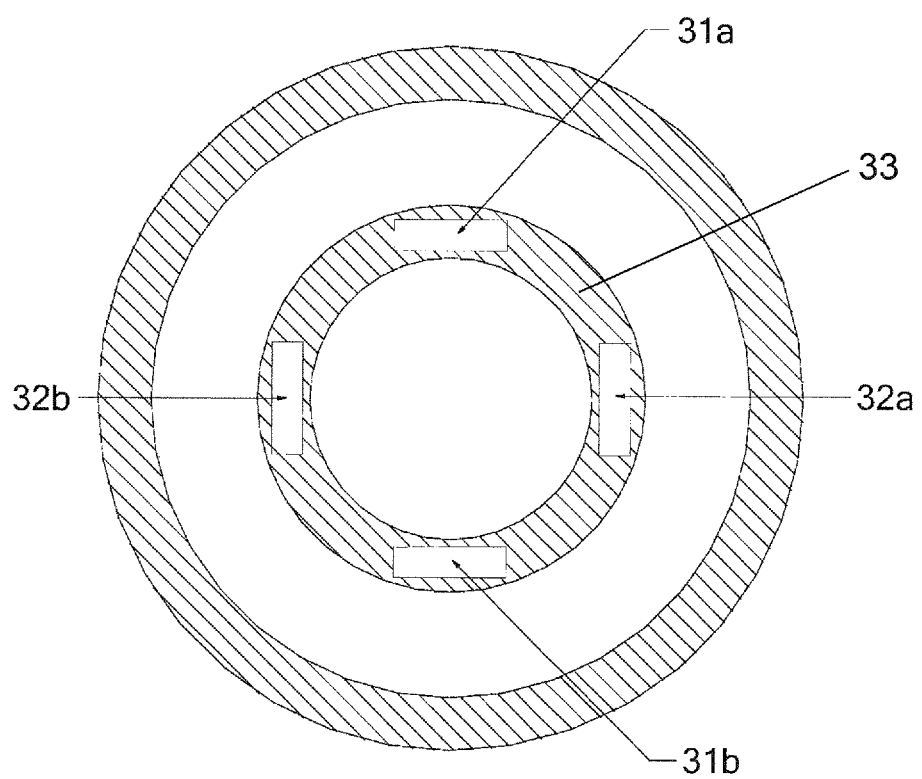
FIG. 3 shows a bottom view of a device comprising electroporate electrodes in accordance with an embodiment of the subject invention.

FIG. 3 shows a bottom view of a device including a second set of electrodes for electroporation in accordance with an embodiment of the subject invention.

According to certain embodiments, electrodes are placed as physically close to the tissue as possible. The arrangement of each additional set of electrodes for the electroporation involves placing the pairs on opposing sides of the area of delivery. Using the concentric device configuration as an example, FIG. 3 shows an arrangement of two sets of additional electrodes. The first additional set of electrodes 31*a* and 31*b* and the second additional set of electrodes 32*a* and 32*b* can be slightly recessed into a wall of the interior chamber to preclude direct electrode to tissue contact. The electrodes 31*a*, 31*b*, 32*a*, and 32*b* can be recessed into the interior wall 33 of the device. In a further embodiment, a protective layer (not shown) can be disposed on the exposed surface of the electrodes between the electrodes and the tissue being contacted. The electrical circuit between the tissue and the electrode can be completed with a compatible gel, buffer, or bodily fluid. The pulses can occur between any positive (+) and negative (−) electrode plate. For example, a pulse can occur between the positive electrode 31*a* of the first additional set and either the negative electrode 31*b* of the first additional set or the negative electrode 32*b* of the second additional set. In addition, a pulse can occur between the positive electrode 32*a* of the second additional set and either the negative electrode 31*b* of the first additional set or the negative electrode 32*b* of the second additional set. Programming (with a control processor) can be used to control pulse length, duration, and frequency. Other designs could include an array of electrodes greater than the four depicted.

The electrodes preferably are made of a material or composite material, and geometry, to prevent the accumulation of electrolytically generated gasses from accumulating and thereby obscuring that portion of the electrode from the buffered phase it is embedded or immersed in (i.e., the gasses form an insulating region, creating perturbations in the electric field).

In one embodiment, the geometry of the electrodes includes a ring shape. Embodiments using geometry to minimize gas accumulation utilize geometries having minimal planar characteristics in order to minimize or avoid gas accumulation, which is known to occur on solid, planar/plate-shaped electrodes. In another embodiment, minimizing accumulation of the gasses can be accomplished by plating a buffering agent onto the electrode. For example, the electrodes can be made of silver with silver chloride plating. At the silver chloride electrode, the H+ acid that is generated is kept in solution as HCl instead of bubbling out as $H_2$ or forming $H_3O+$.

In certain embodiments, the electrodes can be outfitted with a component that can agitate the electrode to free any accumulated electrolytically generated gasses.

The electrodes can be separated from the subject or tissue by multiple distinct phases with properties conducive to distinct functions. An embodiment can include buffering phases in contact with the electrodes that possess properties conducive to neutralizing the electrolytically generated acid and base species.

Another embodiment can include a delivery phase with properties conducive to introducing the deliverable into the tissue of interest, including, but not limited to the addition of chemical penetrants, bioavailability enhancers, and analgesics. The delivery phase can be of small, or minimum, volume to reduce the distance that the deliverable travels prior to being introduced into the tissue of interest, where the minimum volume is constrained by the solubility of the deliverable in the delivery phase and by the topography of the surface of the tissue of interest. For example, with two equal volumes with variable radii, one small and the other long, the volume with the wider radius has a lower column height and therefore a shorter distance between the "top" of the volume to the tissue. Additionally, if a homogenous delivery pattern is desired into a tissue with many pits or sulci/gyri (like the surface of the brain or finger prints), the volume can be sufficient to fill the low points and still submerge the peaks, to reduce, or prevent, a heterogeneous delivery pattern with the peaks omitted. In one embodiment, the delivery can be targeted to the pits or sulci by reducing the volume of the solution. In a specific embodiment targeting the peripheral annulus of the cornea (i.e. the limbus), the central cornea can be precluded (and the limbus targeted) by reducing the volume of the solution.

The device can include a means of immobilizing the device onto the tissue of interest. Examples include, but are not limited to, vacuum induced immobilization, adhesive mediated immobilization, straps, bands, external brackets, braces, other hardware, screws, sutures, staples, magnets, and immobilization by the patient or care provider physically holding the device with sufficient pressure, as means of mating of the device with the tissue of interest.

The electrode to electrode distance can be kept short, or to a minimum, in order to minimize the voltage rating of the power supply, as greater electrode distances require greater voltages to create the same field (ceteris paribus); and to minimize the amount of patient tissue in-between the electrode in order to reduce the pain (fewer neurons affected) and potential triggering of action potentials (which would reduce the chance of muscle twitching). The electrode distance minimum is constrained by the volume and specific buffering capacity (buffering capacity per unit volume) of the buffering phase, which should preferably provide sufficient buffering capacity to avoid chemical burns to the tissue of interest.

The electrode material can be selected based on the rate that the electrode material is oxidized/released and the toxicity of the electrode material. The material can be a conductor or a semi-conductor. For instance, electrodes incorporating copper, pure or in alloy with another material, are not suitable for use in the eye due to the irritation that copper induces. Some suitable electrode materials include platinum and silver/silver chloride electrode systems. The device can be capable of reversing the polarity of the electrodes to allow for delivery of predominantly negatively charged deliverables (e.g., nucleic acids) or the delivery of predominantly positively charged molecules (e.g., some peptides and micro/nano particles).

Figure 4A:
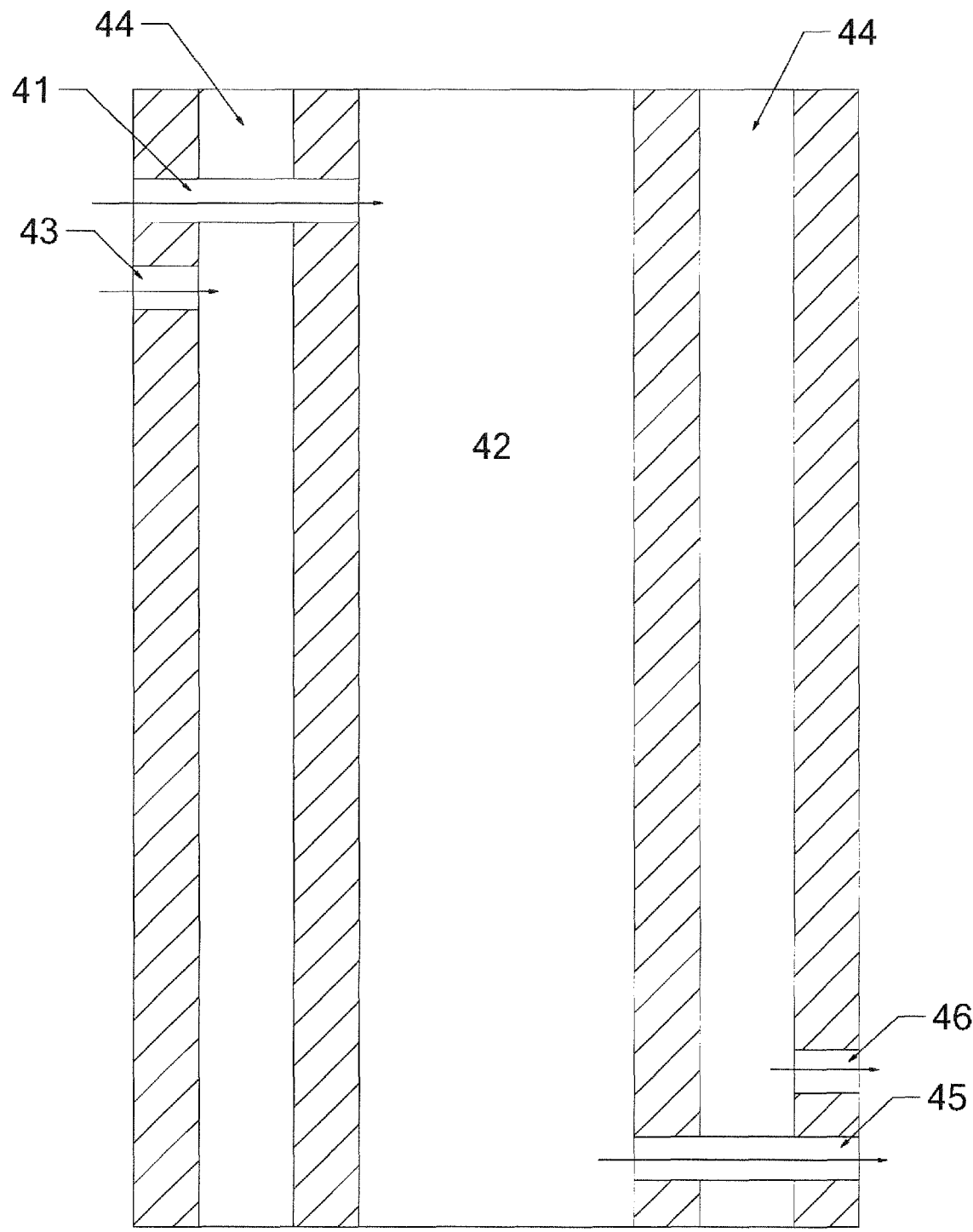
FIGS. 4A and 4B show representative examples of how a concentric chambered device in accordance with certain embodiments of the subject invention can be replenished with fresh buffer.
Figure 4B:
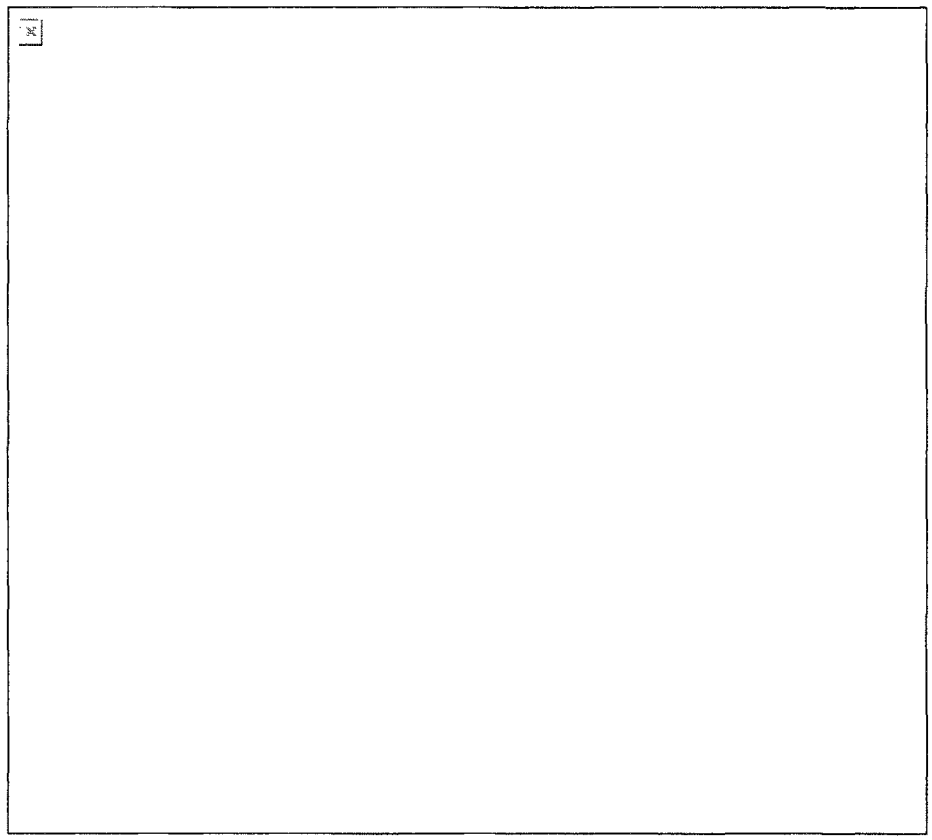

The device can contain a means of circulating fresh mobile phase into and out of the device to prolong dosage, treatment time, and/or buffering capacity. The means of circulating fresh mobile phase into and out of the device can include a small diameter polytetrafluoroethylene (PTFE) or other plastic tubing and a peristaltic pump to communicate the fluid from a reservoir to the delivery device and along another channel, to remove the fluid from the device to a waste reservoir. According to one embodiment, the effluent channel is disposed near the electrodes to aid in removal of the electrolytically acidified or alkalized solution. FIGS. 4A and 4B show examples of how a concentric chambered device could be replenished with fresh buffer. FIG. 4A shows a longitudinal cross-sectional view of a device according to one embodiment and FIG. 4B shows a radial cross-sectional view of a device according to another embodiment.

The conduits to the inner "delivery" chamber can be arranged as spindles connected to the outer wall. The spindles can be hollow to allow either the insertion of a tube, or directly adapted to convey the fluid itself. FIG. 4A illustrates an embodiment where the conduits are parallel. In particular, a first entrance conduit 41 to the inner chamber 42 is parallel to a second entrance conduit 43 to the outer chamber 44, and a first exit conduit 45 from the inner chamber 42 is parallel to a second exit conduit 46 from the outer chamber 44. FIG. 4B illustrates an embodiment where the conduits are orthogonal. In particular, FIG. 4B shows an embodiment where the first entrance conduit 41 and first exit conduit 45 of the inner chamber 42 are orthogonal to the second entrance conduit 43 and second exit conduit 46 of the outer chamber 44. It should be noted that the placement of the conduits with respect to each other are not limited thereto.

The portions of the device that come into contact, or communication, with the tissue of interest should, preferably, be composed of a bio-safe, non-irritating, and non-electrically conductive material. The device may be disposable, reusable, or a hybrid of reusable and disposable components.

Embodiments of the device can be outfitted with sensors to monitor delivery, performance, and/or safety and can adjust the voltage and/or dosing time accordingly. For example, a current detector can be used in order to reduce risk of, or to prevent, electrical shock, a thermostat of any amenable type can be used to prevent overheating, and/or a sensor(s) to monitor the amount of drug delivered can be used.

Figure 5:
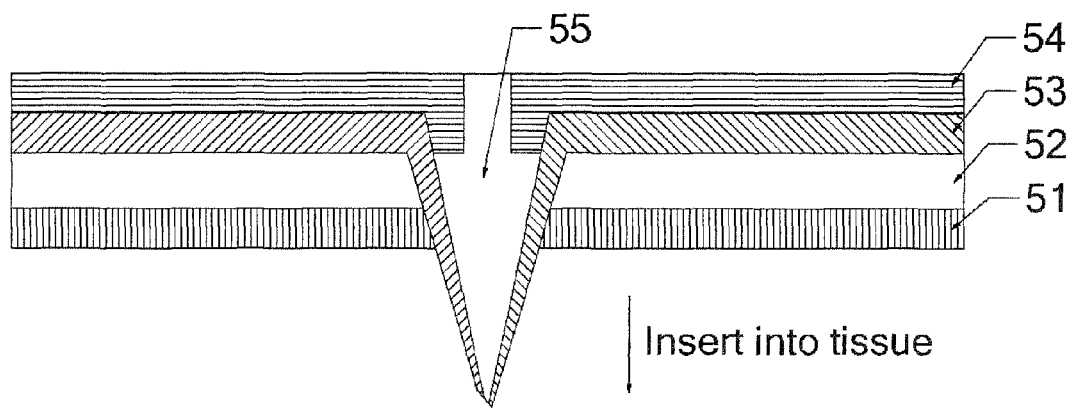
FIG. 5 shows a representation of a device for delivery of macromolecules having an array of hollow tissue penetrating needles in accordance with an embodiment of the subject invention.

The device may incorporate an array of hollow tissue penetrating needles (microneedles) through which the electric field can selectively deliver the deliverable into the mechanically disrupted tissue. FIG. 5 shows a representation of a device using an array of hollow tissue penetrating needles. Referring to FIG. 5, a single needle is illustrated, but the device can include a singular or multidimensional array of the illustrated needle. A first layer 51 can be used to contact a tissue. The first layer 51 separates a first electrode 52 from the tissue, and can be used to store a buffer. The first layer 51 can be a porous material that can allow for conformity to the tissue. In one embodiment, the porous material is a gel with a buffer. The first electrode 52 can be a positive electrode of the device. The electrode 52 can be a conductive sheet or film with an aperture for the needle 53 to extend through. In another embodiment, the electrode 52 can be surrounded by a buffer. In one such embodiment where the buffer surrounding the electrode 52 is contained within a gel, matrix, sponge, mesh, or other porous material, the first layer 51 can be omitted or a biphasic chamber can be provided (formed of a first porous material for the first layer 51 and a second porous material surrounding the electrode 52). The needle 53 can be made of a non-conducting material or a low-conducting material so long as the needle does not cause a short between the electrodes or conduct current improperly into the tissue. The needle 53 can be a flexible needle or a rigid needle, depending on application. A second electrode 54 can be disposed on the needle 53 and can extend a distance within the interior 55 of the needle 53. The second electrode 54 can be a negative electrode when the first electrode 52 is the positive electrode of the device. The polarity of the first and second electrodes 52, 54 can be reversed for the delivery of cations. In operation, a deliverable and a suitable buffer can be placed in the needle. The buffer can be disposed so as to contact the second electrode 54. Although not shown, a suction device can be included at the outer circumference of the array of tissue penetrating needles to keep the delivery device in place.

Figure 6A:
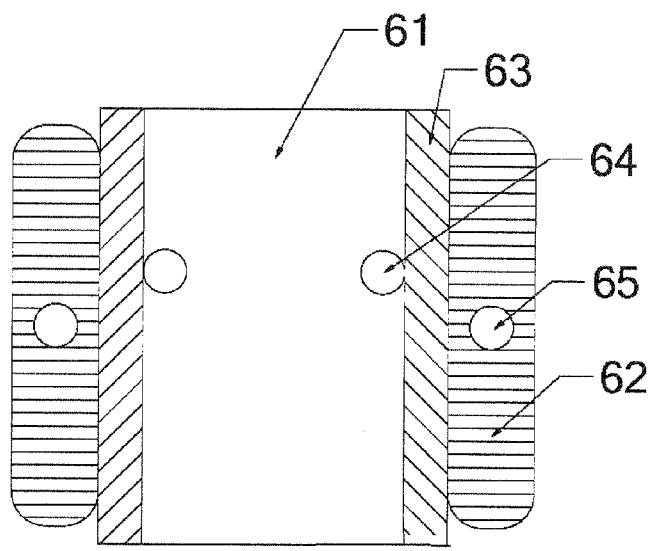
FIGS. 6A-6C show longitudinal cross-sections of configurations for a two chamber device for delivery of macromolecules according to certain embodiments of the subject invention.
Figure 6B:
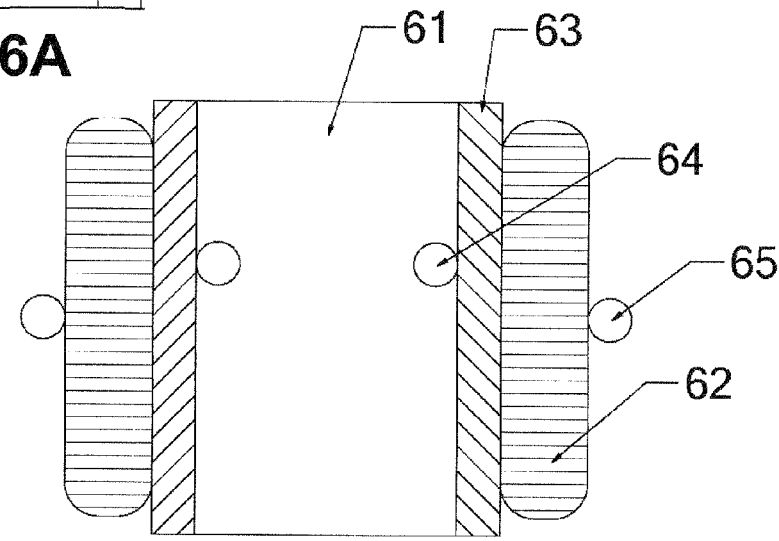
Figure 6C:
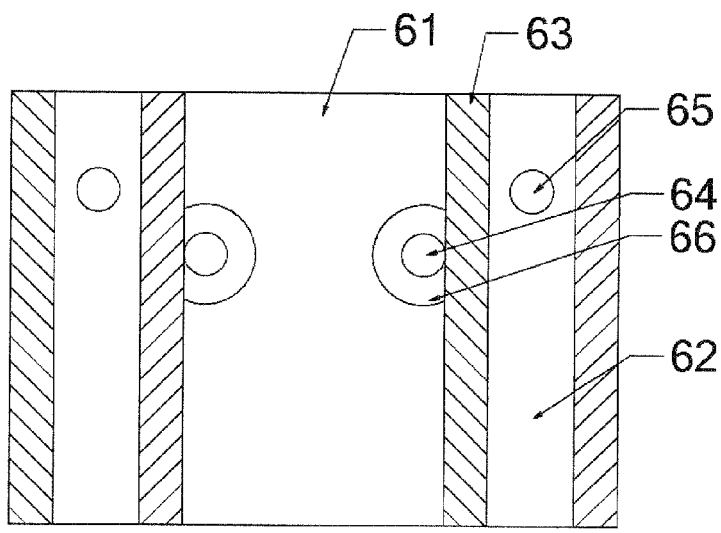

As defined herein, a chamber provides a reservoir for a fluid. The chambers can be provided with one or more walls to define the reservoir or as a sponge, absorbent, resin, matrix, gel, or other porous or capillary containing element that can hold (and allow to release) fluid. FIGS. 6A-6C show longitudinal cross-sections of certain embodiments of concentrically arranged two-chambered devices for delivery of macromolecules. Referring to FIGS. 6A and 6B, a first chamber 61 can be separated from the second chamber 62 by a wall 63. The second chamber 62 can be a porous material attached to the wall 63 with an adhesive. A first electrode 64 can be disposed in the first chamber 61. The second electrode 65 can be disposed in the second chamber 62 (FIG. 6A) or contacting an outer circumference of the second chamber 62 (FIG. 6B). Referring to FIG. 6C, the first electrode 64 can be disposed in the first chamber 61 attached to the wall 63 and protected by a buffer 66 in a matrix or gel. In such an embodiment, the first electrode 64 can be disposed within the first chamber 61 irrespective of the volume of macromolecule delivery medium provided within the first chamber 61. Although the second chamber 62 is shown as being defined by walls, the second chamber 62 (and second electrode 65) can be configured as shown in FIG. 6A or 6B.

The device can be battery, DC, and/or AC powered. An array of electrodes can be used, where the array of electrodes can be used to steer the deliverable within the tissue of interest by manipulating the electric field at different times. This can be used to avoid certain regions, and/or to target the deliverable to certain regions. The device can be used topically, or can be used internally during surgery to dose into the internal organs. The device can be used to deliver the deliverable into any tissue, cell, membrane, anatomical structure, and cellular or acellular elements (e.g., hair and/or nails).

Figure 7A:
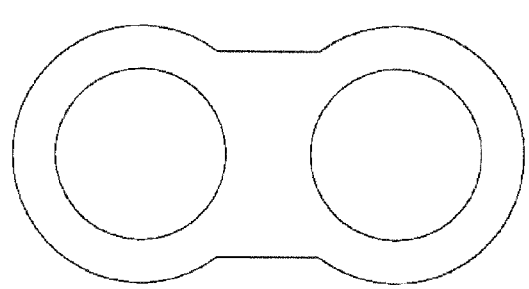
FIGS. 7A-7E show radial cross-sections of configurations for a two-chamber device for delivery of macromolecules in accordance with certain embodiments of the subject invention.
Figure 7B:
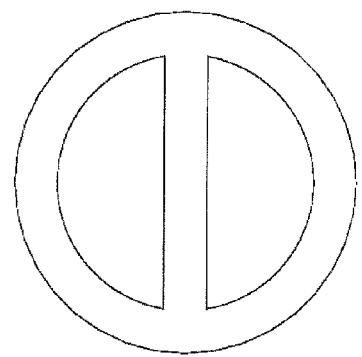
Figure 7C:
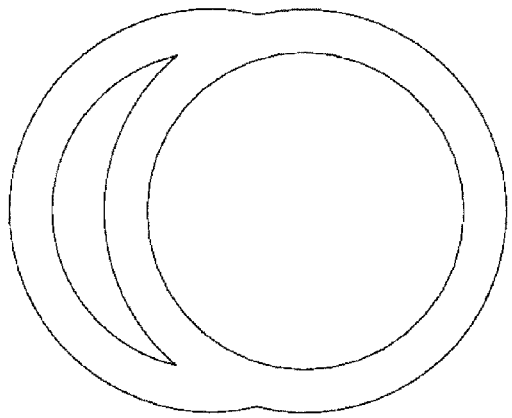
Figure 7D:
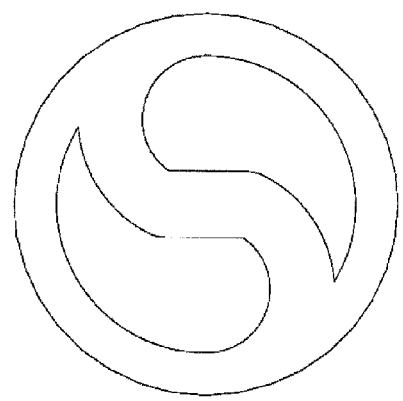
Figure 7E:
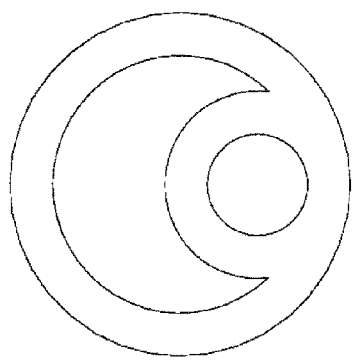
Figure 8A:
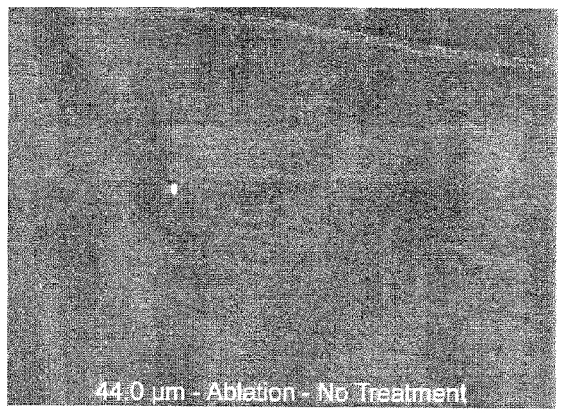
FIGS. 8A-8L show images of ex vivo rabbit eyes that were wounded and then dosed with a green fluorescently labeled 20 nucleotide ssDNA molecule using a device for delivery of macromolecules in accordance with an embodiment of the invention. A blue DAPI stain demonstrates where the cells' nuclei are located.
Figure 8B:
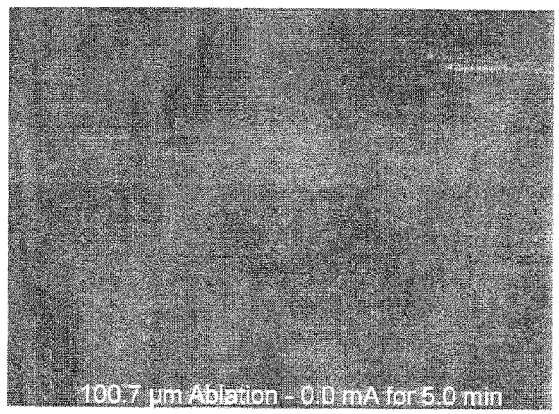
Figure 8C:
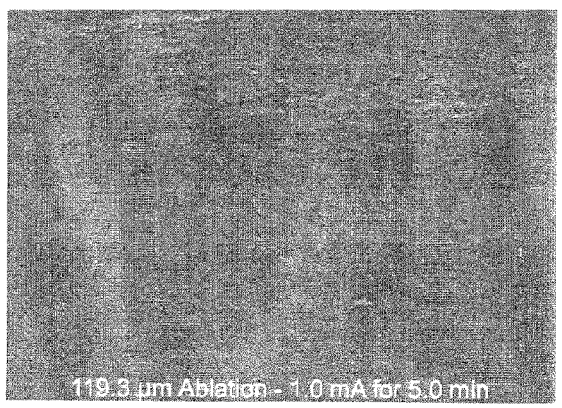
Figure 8D:
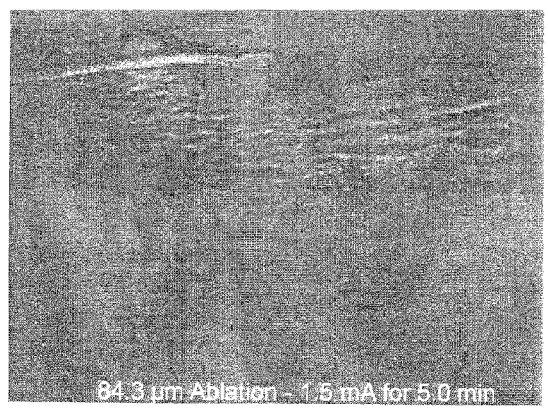
Figure 8E:
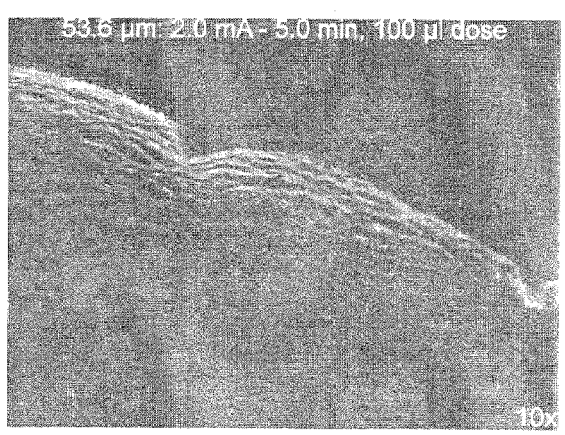
Figure 8F:
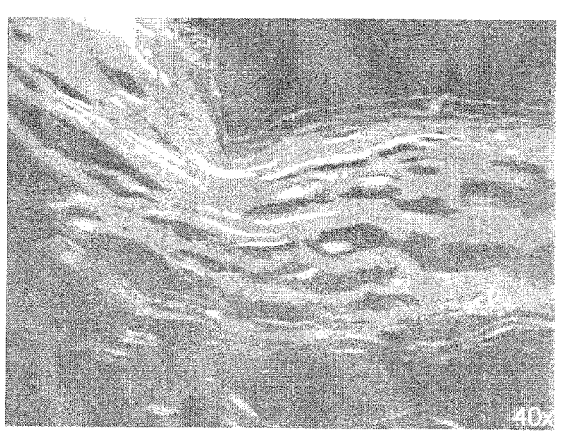
Figure 8G:
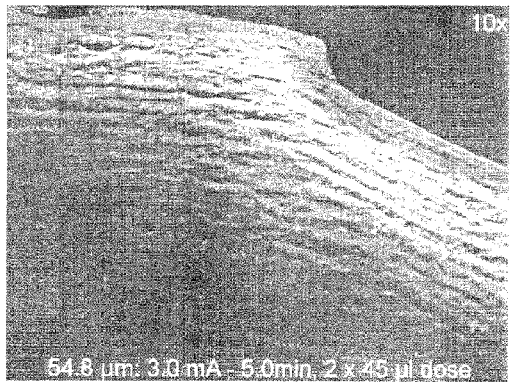
Figure 8H:
Figure 8I:
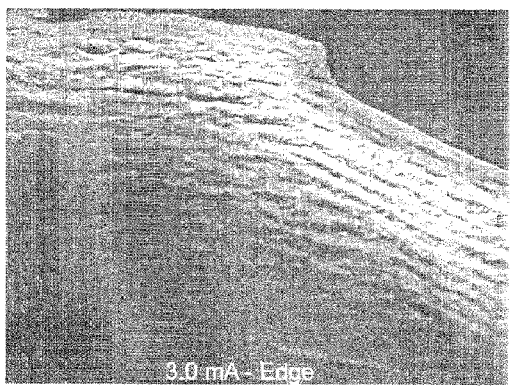
Figure 8J:
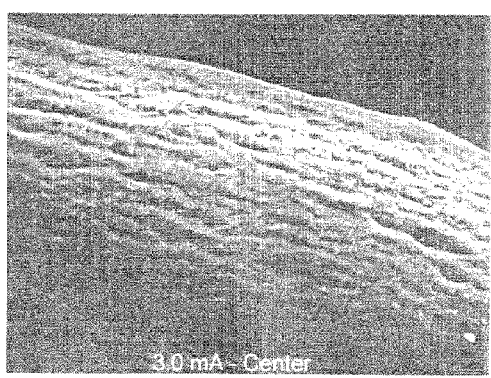
Figure 8K:
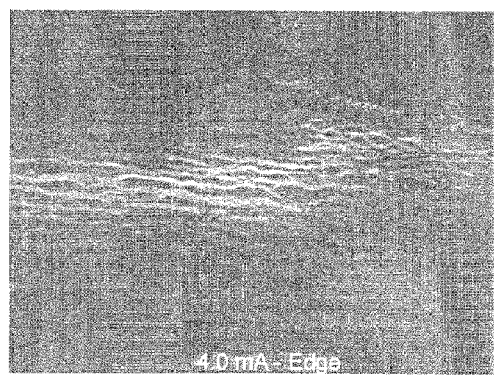
Figure 8L:
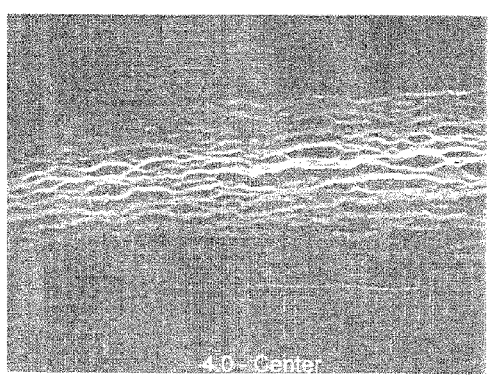

The particular shapes of the chambers of the device for delivery of macromolecules can be adopted to the tissue or modified for a particular distribution of the drug delivery and/or electric field. For example, in one alternative embodiment, such as shown in FIG. 7A, the two chambers side-by-side and sharing a common wall can be used instead of two concentric chambers (such as the concentric device configuration described in embodiments above). The shared wall can be a planar (or straight) wall. In one embodiment, such as shown in FIG. 7B, a tubular chamber can be divided into two chambers by a planar wall extending longitudinally through the tubular chamber. The planar wall can be centrally located on the longitudinal axis of the tubular chamber to create two substantially similarly sized chambers, or off-center to create differently sized chambers. Alternatively, the shared wall can be curved, for example creating a C-shape, such as shown in FIG. 7C, or an S-shape, such as shown in FIG. 7D. In one embodiment, the inner annular chamber of the two concentric chambers of certain embodiments can be arranged so as to abut against the outer wall of the device. The outer wall can be shared at the point where the inner chamber abuts the outer wall, thereby creating a tubular chamber and a chamber having a crescent-shaped cross-section, such as shown in FIG. 7E.

One application for a device using two chambers side-by-side and sharing a common wall is delivery of macromolecules through the skin.

The voltage or current can be varied with time using any profile that is conducive to delivery, including constant, pulsed, ramped, and/or custom voltage or current vs. time profiles. The portions of the device in communication with the tissue can be transparent in order to allow visual assessment of the tissue during treatment. The device can be used externally, or implanted into the body. The device, implanted or otherwise, can be programmed/stand alone, or can be controlled wirelessly by an external control unit. Additionally, the device, implanted or otherwise, can be controlled by a trigger, such as, but not limited to, body temperature, the level of a biomarker in a bodily fluid, time of day, and/or presence/absence of light.

Example: Delivery of Anti-Scarring Drugs into the Cornea Following Wounding

Prior to conducting the in vivo rabbit studies, a delivery efficacy experiment was conducted in ex vivo rabbit eyes obtained from an abattoir. The eyes were centrally wounded with an excimer laser creating a 6.0 mm diameter wound. A 20 nucleotide single stranded DNA with a green fluorescent target (5'-carboxy fluorescein) was used as it has similar charge, mass, and size as the anti-scarring antisense DNA oligonucleotides (ASOs) used in treatment. Currents of 0.0 mA, 1.0 mA, 1.5 mA, 2.0 mA, 3.0 mA, and 4.0 mA were applied for 5.0 min. The results are depicted in FIGS. 8A-8L. A blue DAPI stain demonstrates where the cells' nuclei are located. As illustrated by comparing FIG. 8A with FIG. 8B, no oligonucleotides are detectable following topical application without current. Referring to FIGS. 8C-8H, trace amounts of oligonucleotides are shown delivered into the wounded eye at currents of 1.0-2.0 mA. Referring to FIGS. 8I-8L, significant amounts of oligonucleotide, as demonstrated by the center total fluorescent mass being within the tissue, occurs beginning at 3.0 mA.

Rabbit studies were conducted, generating data of the effects of anti-scarring ASOs delivered using an iontophoresis drug delivery device in accordance with an embodiment of the invention.

During the experiment, certain rabbits were treated with an anti-scarring drug using the iontophoresis drug delivery device according to an embodiment of the invention and certain rabbits were topically treated with the anti-scarring drug by using the iontophoresis drug delivery device without application of current.

For application of the anti-scarring drugs in both the topical and iontophoretically treated eyes, the cup was loaded with buffer and drug, and then the device with buffer and drug was held in place for 5 minutes. The subjects receiving iontophoresis (3 rabbits, 6 eyes, 3 treatment eyes, 3 mock treatment eyes), received 4.0 mA of current through the electrodes for 5 minutes using a cup with an inner diameter of 1.1 cm.

Figure 9:
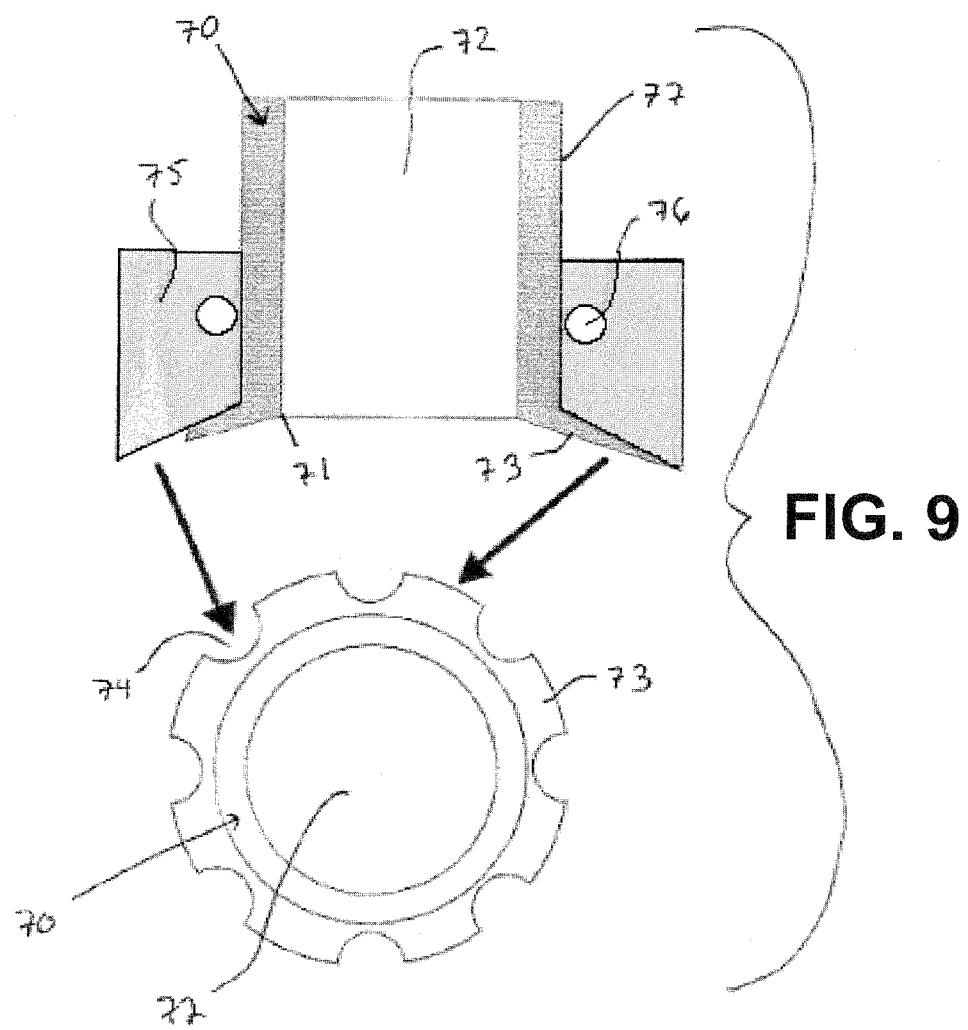
FIG. 9 shows a device for delivery of macromolecules in accordance with an embodiment of the invention.

FIG. 9 shows a representation of the device for delivery of macromolecules used in this example, which incorporates a concentric chambers design. In particular, FIG. 9 provides the side cross-sectional view of the lower portion of the cup and the corresponding top-down view. For this prototype, a cup 70 having a flanged distal end 71 provides the chamber 72 for the delivery medium. The flange portion 73 has a flower-like shape providing openings 74 for contact of media at the outer side of the cup to a tissue. In this embodiment, the reservoir 75 for the receivable medium is configured using a gauze wrapped around a positive, ring-shaped electrode 76. The electrode 76 is fixed in position at the outer side 77 of the cup 70. The electrode can be held in place with a strip of latex or nitrile rubber. The notches (or openings) 74 cut out of the flange 73 at the distal end 71 of the cup 70 allow the gauze/buffer 75 to be placed into communication with the tissue. The gauze was arranged coincident with the notched flower-like flange.

For drug delivery, the distal end 71 of the cup 70 was placed on the eye, the gauze was soaked with buffer (25 mM HEPES pH 7.9), the cup was filled with buffer (25 mM HEPES pH 6.8). In addition, the drug was sunk to the bottom and onto the tissue using a density adding agent and the negative electrode was placed in the cup (ring-shaped, not shown). Here, the density adding agent used was dextrose and/or sucrose. The electricity was applied at a current of 4.0 mA for 5.0 min.

Figure 10:
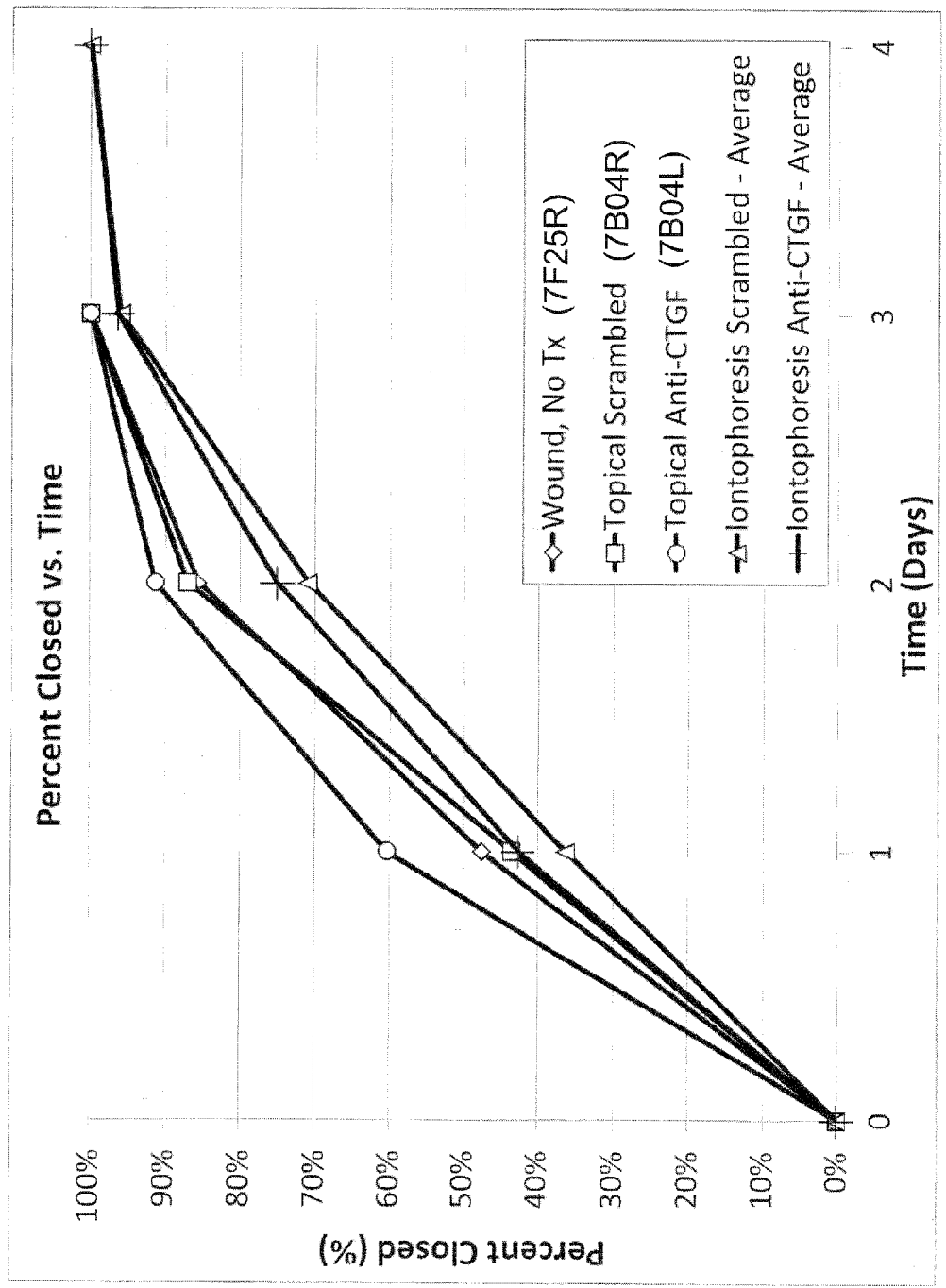
FIG. 10 shows a plot of percent closure of a wound over time, comparing a wound having no treatment to topical application of scrambled oligonucleotides and anti-CTGF ASO and iontophoresis of scrambled oligonucleotides and anti-CTGF ASO using the device for delivery of macromolecules such as shown in FIG. 7 in accordance with an embodiment of the invention.

FIG. 10 shows a plot of percent closure of a wound over time, comparing a wound with no treatment (dash with diamond indicator) to topical application of scrambled ASOs (dash with square indicator) and anti-CTGF ASOs (dash with circle indicator) and iontophoresis of scrambled ASOs (solid with triangle indicator) and anti-CTGF ASOs (solid with line indicator) using the device for delivery of macromolecules in accordance with an embodiment of the invention. The difference in treatments appears to be neither clinically nor statistically significant, meaning that the treatment does not impair wound re-epithelialization. The iontophoresis may be marginally responsible for the 1 day delay. The percentage closed (% Closed) was calculated using the following relationship:

$$\% \text{ Closed} = \frac{\text{Initial Area} - \text{Measured Area}}{\text{Initial Area}}.$$

Figure 11:
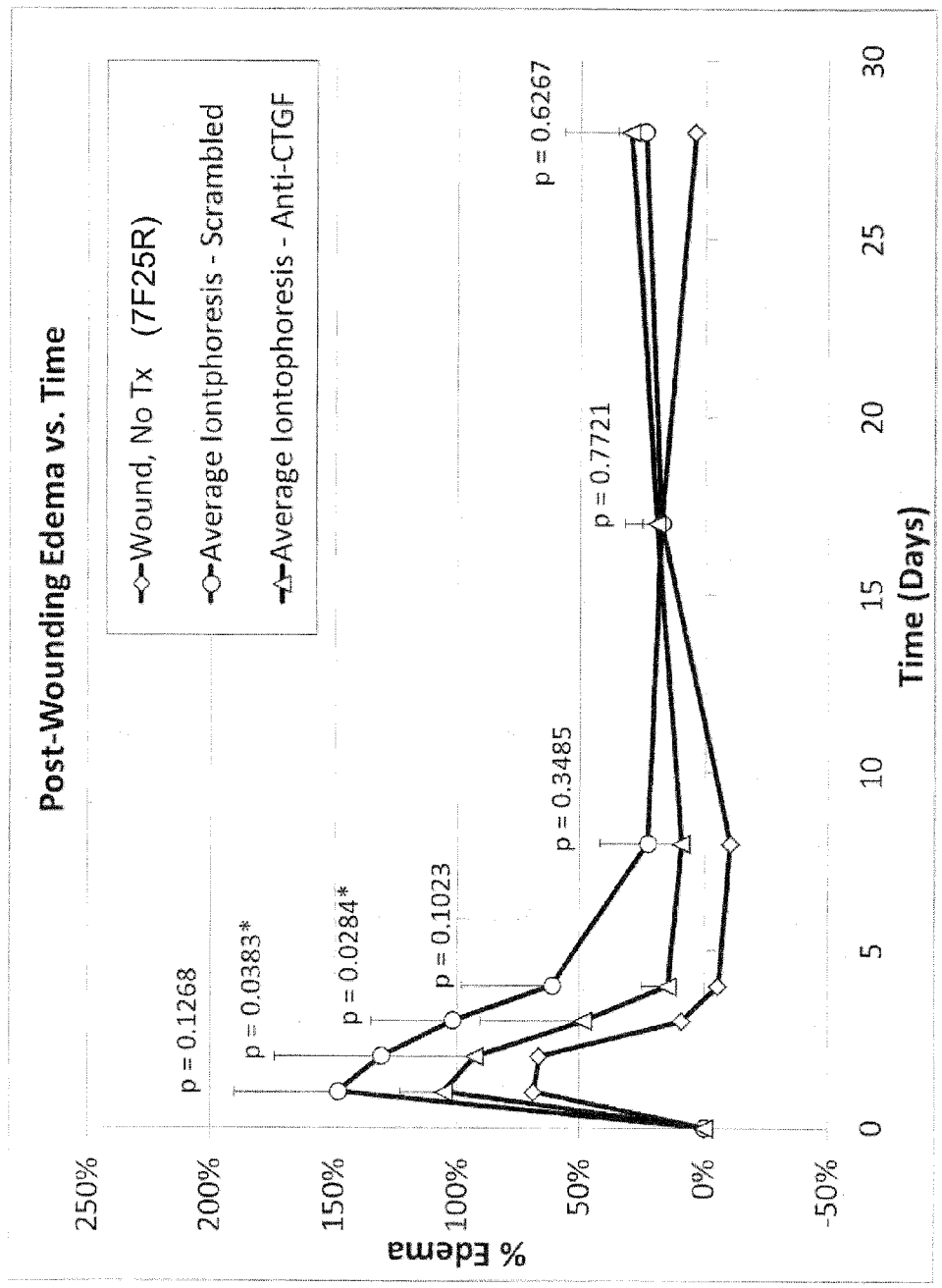
FIG. 11 shows a plot of percent post-wounding edema over time, comparing a wound with no treatment to iontophoresis of scrambled oligonucleotides and anti-CTGF ASO using the device for delivery of macromolecules such as shown in FIG. 7 in accordance with an embodiment of the invention.

FIG. 11 shows a plot of percent post-wounding edema over time, comparing a wound with no treatment to iontophoresis of scrambled oligonucleotides and anti-CTGF ASO using the device for delivery of macromolecules in accordance with an embodiment of the invention. The difference in corneal thickness is normalized to post-wounding thickness. The dextrose solution used to irrigate the cornea may be causing additional post wound swelling. FIGS. 12A-12D show images of the eyes of a control rabbit (FIGS. 12A and 12B) and a rabbit receiving iontophoretically delivered scrambled ASO (FIG. 12C), or anti-CTGF ASO (FIG. 12D). In particular, FIG. 12A shows a rabbit cornea that is wounded with no treatment, FIG. 12B shows a rabbit cornea that is not wounded and has no treatment applied, FIG. 12C shows a rabbit cornea after a treatment with scrambled ASO, and FIG. 12D shows a rabbit cornea after treatment with anti-CTGF ASO. It should be noted that this example experiment is a pilot experiment and should not be taken as an indication of particular or quantitative efficacy for the prototype device.

Example: Delivery of Macromolecules into the Foot

Figure 13:
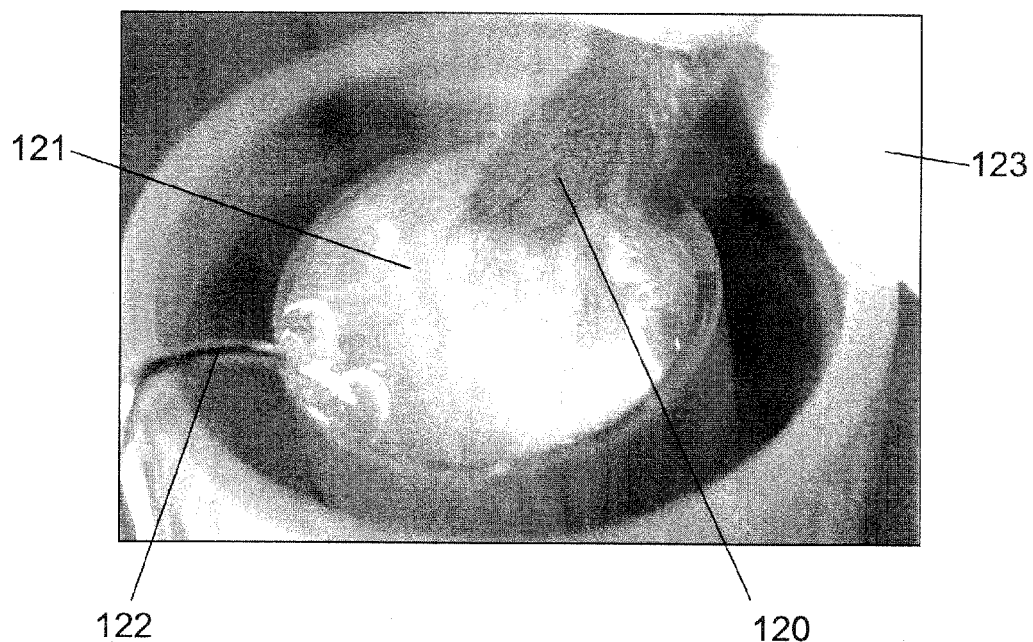
FIG. 13 shows a photograph of an implementation for delivery of macromolecules in accordance with another embodiment of the subject invention.

FIG. 13 shows a photograph of an implementation for delivery of macromolecules in accordance with another embodiment of the subject invention. The device for delivery of macromolecules can be provided as a foot-bath for treating the plantar surface of the foot and/or toe nails. Referring to FIG. 13, which shows an experimental prototype, a mouse foot 120 is shown submerged in a first chamber 121 filled with delivery medium and an electrode 122. A second chamber is provided as a soaked gauze 123. The second electrode is not shown in the photograph, but is located further up on the leg and contacts the soaked gauze 123.

Figure 14A:
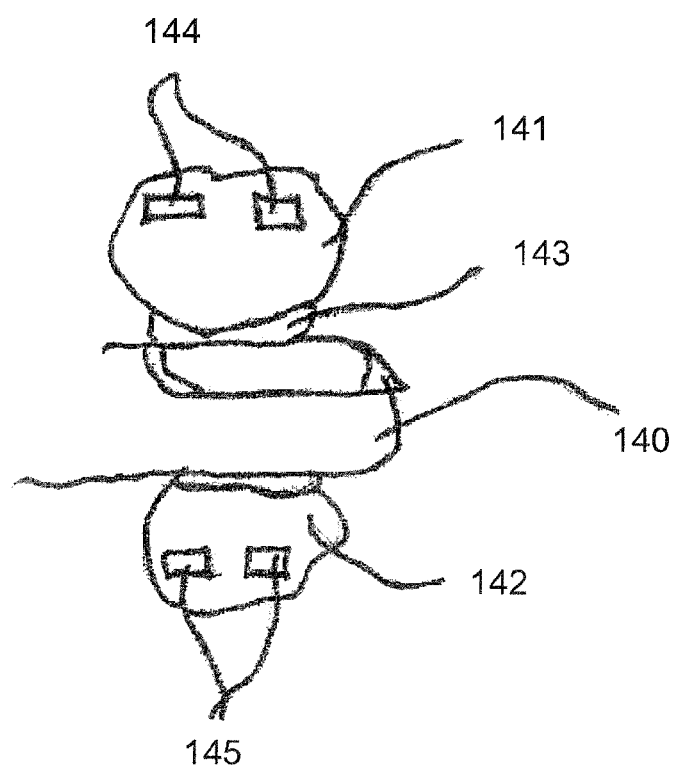
FIGS. 14A and 14B show representations of a device for electromotive delivery of macromolecules into tissue in accordance with one embodiment of the subject invention.
Figure 14B:
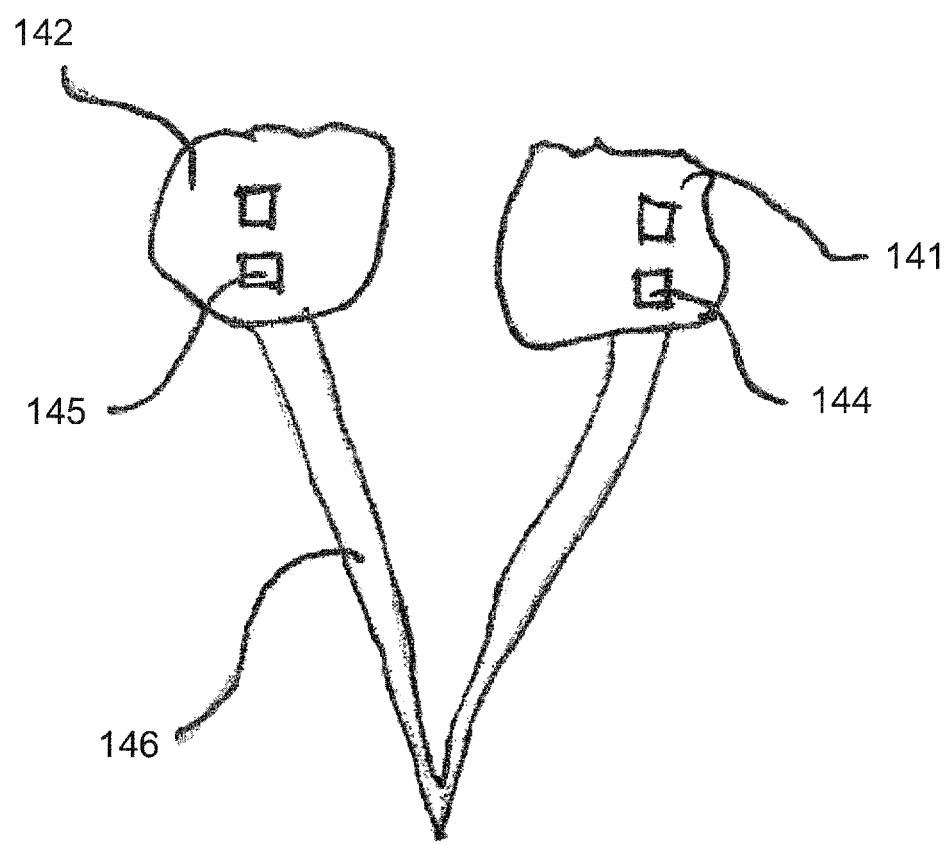

FIGS. 14A and 14B show representations of a device for electromotive delivery of macromolecules into tissue in accordance with another embodiment of the subject invention. A method of delivery using the device such as shown in FIGS. 14A and 14B can be referred to as a nanodrop method. Referring to FIG. 14A, a porous material can be used for the first chamber 141 and the second chamber 142 of the device. The porous material can be, for example, rayon or cotton or other sponge or gel-like material. The first chamber 141 can be placed such that macromolecules in a delivery medium in the first chamber can, for example, contact a toe 140. The first chamber 141 and/or the second chamber 142 can be directly applied to the toe 140, or allowing a capillary column 143 to form between the device and the subject tissue. One or more first electrodes 144 can be disposed on or in the first chamber 141 and one or more second electrodes 145 can be disposed on or in the second chamber 142. As shown in FIG. 14B, a connector 146 can be used to connect the first chamber to the second chamber. The connector 146 is non-conductive or minimally conductive so as to not adversely affect the electric fields generated by the first and second electrodes 144 and 145. In one embodiment, the connector 146 can be tongs or a clip that can be used to hold the device in place. In another embodiment, the connector 146 can have elastic properties so as to allow a tissue between the first and second chamber 141, 142 to deform the connector 146 while maintaining pressure on the tissue. Although the first chamber 141 and the second chamber 142 are shown in FIG. 14A as being on opposing sides of tissue, embodiments are not limited thereto. For example, the first and second chamber can be side-by-side on a surface of the tissue.

All patents, patent applications, provisional applications, and publications referred to or cited herein are incorporated by reference in their entirety, including all figures and tables, to the extent they are not inconsistent with the explicit teachings of this specification.

Any reference in this specification to "one embodiment," "an embodiment," "example embodiment," etc., means that a particular feature, structure, or characteristic described in connection with the embodiment is included in at least one embodiment of the invention. The appearances of such phrases in various places in the specification are not necessarily all referring to the same embodiment. Further, when a particular feature, structure, or characteristic is described in connection with any embodiment, it is submitted that it is within the purview of one skilled in the art to utilize or combine such feature, structure, or characteristic in connection with other ones of the embodiments.

It should be understood that the examples and embodiments described herein are for illustrative purposes only and that various modifications or changes in light thereof will be suggested to persons skilled in the art and are to be included within the spirit and purview of this application. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A device for electromotive delivery of macromolecules, the device comprising:
   a first chamber having a first distal end for contact with a tissue of a patient, wherein the first distal end of the first chamber allows a macromolecule delivery medium in the first chamber to contact the tissue of the patient;

a second chamber having a second distal end for contact with the tissue of the patient, wherein the second distal end of the second chamber allows a receivable medium in the second chamber to contact the tissue of the patient;

a connector connecting the first chamber and the second chamber together;

a first electrode within the first chamber;

a second electrode within the second chamber; and a voltage source, wherein the voltage source is capable of applying a voltage between the first electrode and the second electrode.

2. The device according to claim 1, wherein the second chamber is separated from the first chamber by a separation wall.

3. The device according to claim 1, wherein the connector comprises at least one spoke contacting a first wall of the first chamber and a second wall of the second chamber.

4. The device according to claim 1, wherein the connector comprises an adhesive.

5. The device according to claim 1, further comprising the macromolecule delivery medium in the first chamber in contact with the tissue of the patient, wherein the first electrode in contact with the macromolecule delivery method.

6. The device according to claim 1, further comprising the receivable medium in the second chamber in contact with the tissue of the patient, wherein the second electrode in contact with the receivable medium.

7. The device according to claim 1, wherein the second electrode is disposed at an outer circumference of the second chamber.

8. The device according to claim 1, wherein the first chamber is tubular, and wherein the second chamber is annular and concentric to the first chamber.

9. The device according to claim 1, wherein the second chamber is tubular, and wherein the first chamber is annular and concentric.

10. The device according to claim 9, wherein the first suction device comprises a vacuum chamber within a wall of the first chamber to allow a vacuum to be applied to the suction device.

11. The device according to claim 1, wherein the first chamber comprises a first wall separating inside the first chamber from outside the first chamber; and a first suction device capable of creating a first vacuum seal between a first distal end of the first wall of the first chamber and the tissue of the patient.

12. The device according to claim 1, wherein the first electrode and the second electrode are each an individual monolithic electrode.

13. The device according to claim 1, wherein the first electrode comprises a first array of electrodes in the first chamber, and wherein the second electrode comprises a second array of electrodes in the second chamber.

14. The device according to claim 13, wherein a selected electrode of the first array has a separate voltage connection from another electrode of the first array such that a different voltage is allowed to be applied to the selected electrode of the first array than that applied to the another electrode of the first array, and wherein a selected electrode of the second array has a separate voltage connection from another electrode of the second array such that a different voltage is allowed to be applied to the selected electrode of the second array than that applied to the another electrode of the second array.

15. The device according to claim 1, further comprising a sensor to monitor at least one of macromolecule delivery, current, and temperature.

16. The device according to claim 1, wherein the first chamber comprises a hollow tissue penetrating needle, the device comprising a plurality of hollow tissue penetrating needles, wherein the first electrode is disposed at an upper portion of the plurality of hollow tissue penetrating needles such that upon generating an electric field using the first electrode and the second electrode, the electric field directs a macromolecule delivery medium in the hollow tissue penetrating needles into the patient.

17. The device according to claim 16, wherein the second chamber comprises a porous layer disposed around a portion of the hollow tissue penetrating needle, and wherein the second electrode is a plate electrode disposed at an upper portion of the second chamber such that the porous layer protects the patient from the second electrode.

18. The device according to claim 16, wherein the second chamber is a biphasic chamber, wherein the biphasic chamber comprises:

a first porous layer disposed around a first portion of the hollow tissue penetrating needle, wherein the second electrode is disposed within the first porous layer, and a second porous layer disposed around a second portion of the hollow tissue penetrating needle, the second portion being below the first portion such that the second porous layer is allowed to contact the patient.

19. The device according to claim 16, wherein the second chamber comprises a porous layer disposed around a portion of the hollow tissue penetrating needle, and wherein the second electrode is disposed within the porous layer.

20. The device according to claim 16, wherein the second chamber comprises a gel, a sponge, or a matrix configured to hold the receivable medium.

21. The device according to claim 1, further comprising a third electrode and a fourth electrode disposed at the first distal end of the first chamber for electroporation of macromolecules of the macromolecule delivery medium into the patient.

22. The device according to claim 1, further comprising a second medium in the first chamber, wherein the second medium is not in contact with the tissue of the patient, wherein the first electrode is in contact with the second medium and the second medium is in contact with the macromolecule delivery medium, wherein the first electrode is not in contact with the macromolecule delivery medium.

23. A method of delivering macromolecules to a tissue, the method comprising:

contacting a macromolecule delivery medium disposed in a first chamber of a delivery device to a tissue of a patient, and contacting a receivable medium disposed in a second chamber of the delivery device to the tissue of the patient, wherein the first chamber and the second chamber are connected together by a connector;

applying a voltage between a first electrode within the first chamber of the delivery device and a second electrode within the second chamber to create an electric field having a contour along a path from the first electrode through the macromolecule delivery medium into the tissue, through a portion of the tissue, out of the tissue, through the receivable medium, and to the second electrode, wherein the electric field causes macromolecules from the macromolecule delivery medium to be delivered to the tissue.

24. The method according to claim 23, wherein the first electrode is in contact with the macromolecule delivery medium, wherein the second electrode is in contact with the receivable medium.

25. The method according to claim 23, further comprising:
providing a second medium to the first chamber of the delivery device at a second portion of the first chamber, wherein the second medium is in contact with the macromolecule delivery medium, wherein the second medium is not in contact with the tissue of the patient, wherein the first electrode is in contact with the second medium,
wherein the second medium prevents the first electrode from directly contacting the macromolecule delivery medium.

26. The method according to claim 25, wherein the second medium and the receiving medium each comprise buffering phases conducive to neutralizing electrolytically generated acid and base species.

27. The method according to claim 23, wherein the receiving medium comprises a buffering agent bound to a gel or matrix.

28. The method according to claim 23, comprising using a macromolecule delivery medium having multiple phases of varying densities such that macromolecules in the macromolecule delivery medium sink to lowest portion of the first chamber when disposed in the first chamber.

29. The method according to claim 23, comprising using a macromolecule delivery medium comprising at least one of chemical penetrants, bioavailability enhancers, and analgesics.

30. The method according to claim 23, comprising using a macromolecule delivery medium comprising at least one of plasmids, siRNA, ribozymes, and aptamers.

31. The method according to claim 23, wherein the device comprises an array of first electrodes, wherein applying the voltage between the first electrode and the second electrode further comprises selectively applying voltages to the first electrodes.

32. The method according to claim 31, wherein selectively applying voltages to the first electrodes comprises applying voltages to one of the first electrodes for a first period of time, and applying voltage to another of the first electrodes for a second period of time.

33. The method according to claim 31, wherein selectively applying voltages to the first electrodes comprises applying voltage to one of the first electrodes for a first period of time, and not applying the voltage to the one of the first electrodes for a second period of time.

34. The method according to claim 23, further comprising applying a second voltage between a third electrode and a fourth electrode of the device to electroporate the tissue during and/or after causing the macromolecules from the macromolecule delivery medium to be directed to the tissue.

35. The method according to claim 23, wherein applying the voltage between the first electrode and the second electrode comprises varying a voltage or current of a voltage source.

36. The method according to claim 35, wherein varying the voltage or current of the voltage source comprises applying a pulse, sawtooth, or square wave voltage signal.

37. The method according to claim 23, further comprising:
agitating the first electrode and the second electrode to free any accumulated electrolytically generated gasses.

38. The method according to claim 23, wherein the tissue is a cornea.

39. The method according to claim 23, wherein the macromolecules are delivered to an anatomical structure.

40. The method according to claim 23, wherein the macromolecules are delivered to a cell or a membrane.

41. The method according to claim 23, further comprising;
implanting the delivery device into the patient to contact an internal tissue.

42. The method according to claim 23, further comprising:
adjusting the voltage between the first electrode and the second electrode in response to a signal supplied from a sensor of the delivery device, wherein the sensor of the delivery device detects at least one of the group consisting of: an amount of macromolecules delivered, current, voltage, light, and temperature.

* * * * *